United States Patent [19]

Otero

[11] Patent Number: 5,197,471
[45] Date of Patent: Mar. 30, 1993

[54] DRY MEDICAL ELECTRODE

[76] Inventor: Servio T. A. Otero, P.O. Box 17212, Caracas 1015-A, Venezuela

[21] Appl. No.: 527,811

[22] Filed: May 24, 1990

[51] Int. Cl.⁵ .............................................. A61B 5/04
[52] U.S. Cl. ................................... 128/640; 128/642; 128/798; 128/802
[58] Field of Search ........................ 128/639–642, 128/798, 802

[56] References Cited

U.S. PATENT DOCUMENTS 3,505,993  4/1970  Lewes et al.
4,004,578  1/1977  Palmius.
4,370,984  2/1983  Cartmell ........................... 128/640

FOREIGN PATENT DOCUMENTS 2552035  5/1977  Fed. Rep. of Germany ...... 128/642
2274264  1/1976  France ................................ 128/641
1402205  8/1975  United Kingdom ............... 128/640

Primary Examiner—Lee S. Cohen
Attorney, Agent, or Firm—Dennison, Meserole, Pollack & Scheiner

[57] ABSTRACT

A dry electrode for medical use for recording existent biopotentials on the skin surface and for electrical stimulation of different zones of the human body. The dry electrode comprises a flexible electroconductive plate provided on its bottom side with a plurality of sharp bosses for partial skin penetration. The plate has a corrugated radial extension tongue and two orifices, a first orifice in the center of the plate and a second orifice in the tongue portion. The orifices and the tongue portion allow for different connectors to be utilized, such as a stem with a circular base, a Stillson wrench or a hook type connection. The electrode makes contact on its bottom face with a needle which penetrates and stays anchored within the skin.

11 Claims, 2 Drawing Sheets

A-A

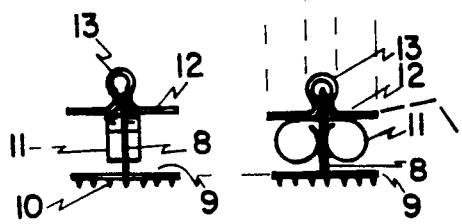
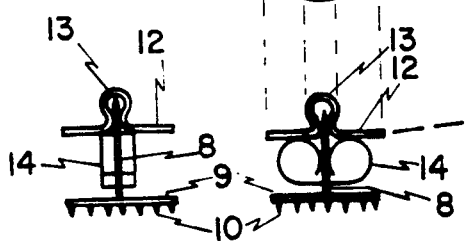
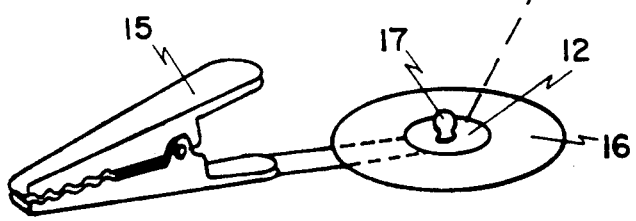
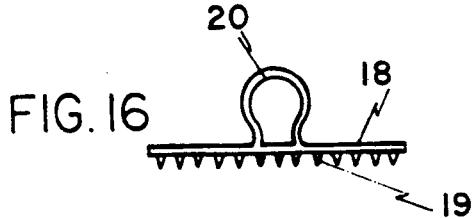
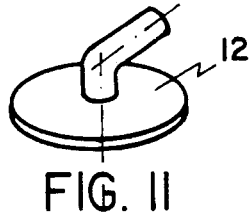
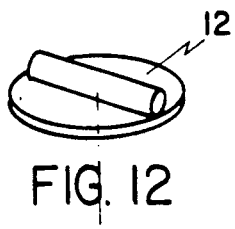
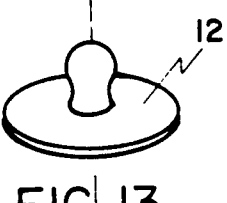
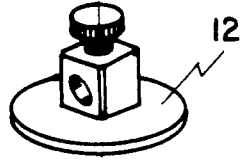
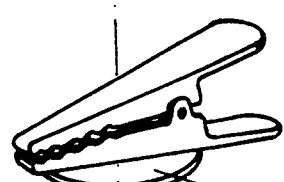

DRY MEDICAL ELECTRODE

BACKGROUND OF THE INVENTION

The present invention is related with the medicine field, specifically; a new dry electrode for recording biopotentials existent on the skin surface of the human being, or for its electrical stimulation.

Dry electrodes of superficial contact without penetration of the skin require signal amplifiers to prevail over the high resistance of the skin corneal layer, and their use makes medical examinations very expensive.

In the art there are also known dry electrodes of partial penetration of the skin, for example in U.S. Pat. No. 3,505,993 where metallic triangular sharp ends adhere firmly to the skin. This dry electrode is rigid, made according to the human body anatomic form, its application being therefore uncomfortable.

Another dry electrode of skin partial penetration is, as shown in the U.S. Pat. No. 4,004,578, which is flexible and adapts itself to any anatomic shape of the human body. However, its aluminum sharp ends in truncated cone form are easily deformed by the pressure exerted over the same to adhere them to the skin. Its adhesive layer, located on the bottom face, acts as an electrical insulant, significantly reducing the electroconductivity of the electrode.

The electrodes known up to now have only one form of connection which is usually disposable together with the electrode. Different monitoring equipment has different connections, therefore all electrodes are not compatible with all equipment. This invention offers the possibility of connecting the electrode to almost any type of monitoring equipment.

SUMMARY OF THE INVENTION

The present invention consists of a dry electrode for recording biopotentials existent on the skin surface of the human being, with various connecting options to be adapted to any signal recording or electrical stimulation equipment.

The electrode comprehends a flexible electroconductive plate, very thin with a plurality of sharp end bosses radially distributed and spaced regularly on its bottom surface, said bosses being of the same conical, pyramidal or truncated characteristics.

On its bottom face the electroconductive plate makes contact with a penetrating needle which has a bent end that anchors it to the skin providing a high electroconductivity for the recording of impulses. The plate has a central hole, a radial extension of the same in the form of a corrugated tongue and another peripheral perforation on the tongue.

The central perforation is for the lower insertion of a stem with an electroconductive circular base with sharp end bosses. The peripheric perforation is for the lower insertion of a hook type connector of electroconductive circular base with sharp end bosses. The corrugated tongue is to fasten a Stillson wrench type connector with non-skid circular base. The electroconductive plate has on its upper face a fastening adhesive of a major area for fixing it to the skin, and on its lower end a protective foil which is detached before using the electrode.

The objective of the present invention is to provide an electrode compatible with any equipment for monitoring and for stimulation between the skin and the electrode.

BRIEF DESCRIPTION OF THE DRAWINGS

FIG. 4 is an upper view of a stem with circular base;

FIG. 5 is a lateral view of the stem of FIG. 4 with circular base, fixed by means of a laminar piece bent down;

FIG. 6 is a front view of the stem of FIG. 5 with circular base, fixed by means of the laminar piece bent down;

FIG. 7 is an upper view of a stem with circular base;

FIG. 8 is a lateral view of the stem of FIG. 7 with circular base, fixed by means of a laminar piece bent up;

FIG. 9 is a front view of the stem of FIG. 8 with circular base, fixed by means of the laminar piece bent up;

FIG. 10 is a perspective view of a Stillson wrench type connector with non-skid circular base;

FIG. 11 is a schematic view of an example of conventional connection;

FIG. 12 is a schematic view of another example of conventional connection;

FIG. 13 is a schematic view of another example of conventional connection;

FIG. 14 is a schematic view of another example of conventional connection;

FIG. 15 is a schematic view of another example of conventional connection;

FIG. 16 is a front view of a hook type connector with sharp end bosses;

DETAILED DESCRIPTION OF THE PREFERRED EMBODIMENTS

Figure 1:
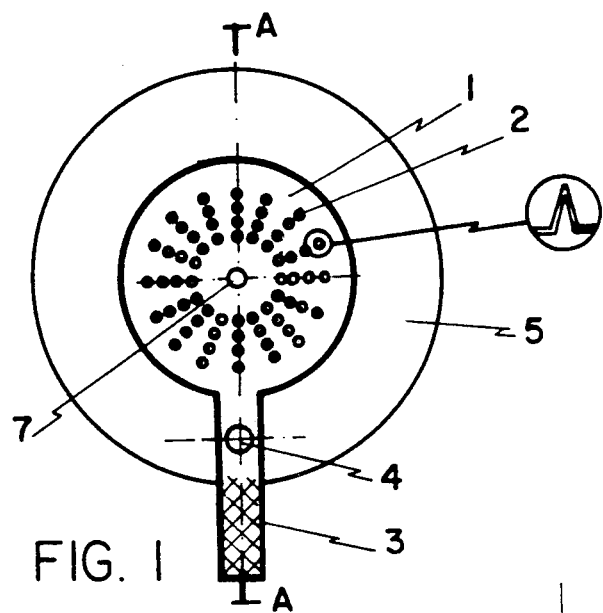
FIG. 1 is a view of an electrode bottom face without protective foil.
Figure 2:
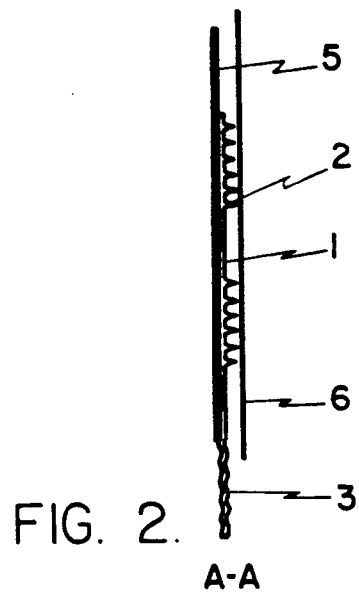
FIG. 2 is a central cross-section view of an electrode with protection foil.
Figure 3:
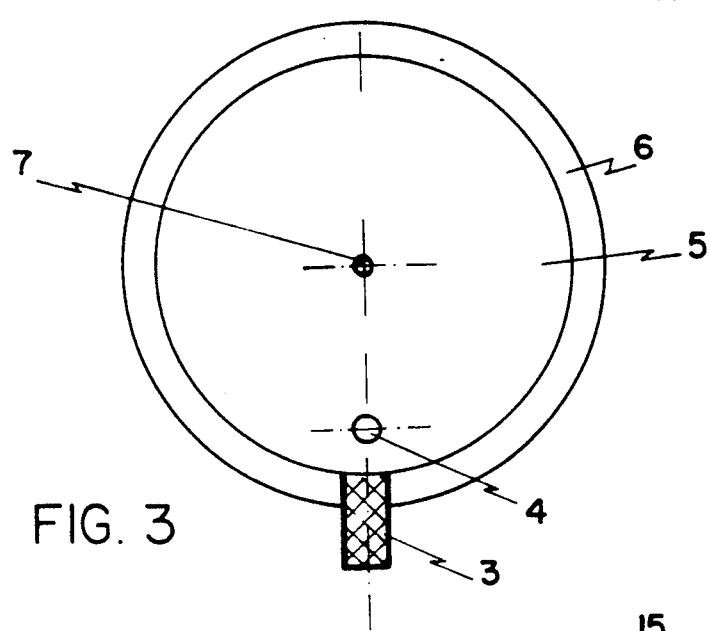
FIG. 3 is a view of an electrode upper face.

FIG. 1 shows a view of the bottom part of an electrode without protective foil, including an electroconductive circular plate 1, with a plurality of sharp end bosses radially aligned and with conical, pyramidal or truncated end shape 2. The electroconductive plate 1 has a radial extension 3 on which there is a peripheral orifice 4. On the center of the circular region there is an area without bosses with a hole in the center 7. The upper face of the electroconductive plate is covered by the fastening circular adhesive 5 of a major area of the electroconductive plate.

On the bottom the electrode has a protective foil 6 slightly bigger than fastening adhesive 5 for easy detaching before use. The central and peripheral holes of the fastening adhesive, and of the electroconductive plate are coincident.

FIGS. 4, 5 and 6 show the stem 8 with circular base 9 provided with sharp end bosses 10, which is inserted in the central orifice of electroconductive plate 1, and is fixed by means of a laminar piece 11 bent down and with its two ends bent in symmetrical spirals towards the inside, leaving a small central space through which the stem 8 passes tightly. The curved laminar piece is folded in its upper region and is joined tangentially to a circular platform to which the upper face can be fixed any conventional connection. Said platform 12 has a central orifice in its bottom face to allow insertion of stem end 8.

FIGS. 7, 8 and 9 show a variant where laminar piece 14 is bent up as shown in FIG. 9. When the two spirals join platform 12 tangentially, the elasticity degree of each spiral is reduced, strengthening the position of stem 8 which passes tightly between them.

FIG. 10 shows a Stillson wrench type connector 15 which has a non-skid circular platform 16 and a conventional connector 17.

FIG. 16 shows a hook type connector 20 having a circular base 18 provided on its bottom face with sharp end bosses 19, the connector adapted for insertion in the peripheric orifice 4 shown in FIG. 1.

Figure 17:
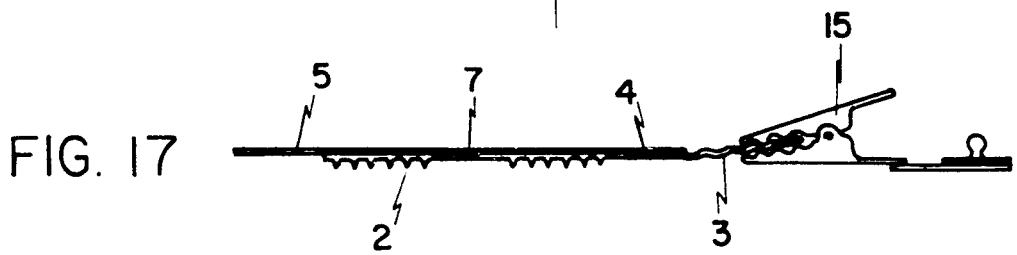
FIG. 17 is a central cross-section view of a dry electrode with Stillson wrench type connector.

FIG. 17 shows the Stillson wrench type connector 15 of FIG. 10 attached to the tongue 3 of a connector, such as is shown in FIG. 1.

Figure 18:
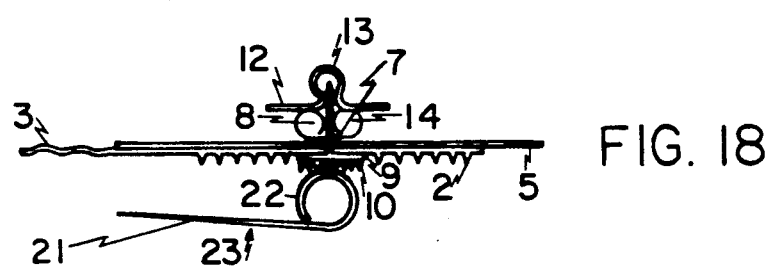
FIG. 18 is a central cross-section view of a dry electrode making contact with a penetration needle which stays anchored to the skin.

FIG. 18 shows the connector of FIG. 1 in conjunction with the connector of FIGS. 7 through 9 and a skin penetration needle. The connector includes a stem 8 which passes through the central orifice of the electrode, stem 8 being secured by a laminar piece 14 and a circular platform 12, with the stem extending up into a connector 13.

At its lower portion, the stem is attached to a circular base 9 provided with sharp end bosses 10.

A penetration needle 23 is anchored to the skin via a skin anchorage end 21. The opposite end 22 of the skin penetration needle is bent on itself and is in contact with the end bosses 10 of circular base 9. The electrode is anchored to the skin utilizing fastening adhesive 5, with end bosses 2 in contact with the skin.

FIGS. 11 through 15 show alternate embodiments for the connecting means used in conjunction with platform 12.

I claim:

1. A medical electrode comprising:
   a circular, flexible, electroconductive first plate having a tongue-shaped radial extension, said plate having top and bottom faces, said bottom face having a plurality of radially aligned sharp end bosses;
   a second plate of greater radius than said first plate and having a surface covered with a fastening adhesive adapted for contacting skin oriented in the same direction as said bosses, said top face contacting said second plate, with said adhesive surrounding the periphery of said first plate;
   a first orifice passing through said first and second plates and in the center of said first plate; and
   a second orifice passing through said first and second plates and in the radial extension of said first plate;
   said electroconductive plate being adapted for contacting a penetrating skin needle through a connector passing through said first orifice or said second orifice, or connected to said radial extension.

2. A medical electrode according to claim 1, wherein the electroconductive plate has sharp end bosses with a pyramidal shape.

3. A medical electrode according to claim 1, wherein the electroconductive plate has sharp end bosses with a truncated cone shape.

4. A medical electrode according to claim 1, wherein the electroconductive plate has sharp end bosses with a truncated pyramidal shape.

5. A medical electrode according to claim 1, wherein the tongue shaped radial extension is corrugated.

6. A medical electrode according to claim 1, additionally comprising a removable protective foil covering said bottom face and said fastening adhesive.

7. A medical electrode according to claim 1, additionally comprising a connector passing through said first orifice or said second orifice or connected to said radial extension.

8. A medical electrode according to claim 7, additionally comprising:
   a bent down laminar piece aligned with said first orifice in said second plate, said laminar piece having lateral ends inwardly folded in symmetrical spirals close to each other at a point tangential to both spirals; and
   a circular platform having a bottom perforation aligned with said first orifice and an electrical connector;
   wherein said connector comprises a circular base with sharp end bosses on one surface thereof and a stem projecting from the other surface thereof, said circular base disposed against the bottom face of said first plate with said stem being inserted sequentially through said first orifice, between the spirals of said laminar piece and through said bottom perforation.

9. A medical electrode according to claim 7, additionally comprising:
   a bent up laminar piece aligned with said first orifice in said second plate, said laminar piece having lateral ends inwardly folded in symmetrical spirals close to each other at a point tangential to both spirals; and
   a circular platform having a bottom perforation aligned with said first orifice and an electrical connector;
   wherein said connector comprises a circular base with sharp end bosses on one surface thereof and a stem projecting from the other surface thereof, said circular base disposed against the bottom face of said first plate with said stem being inserted sequentially through said first orifice, between the spirals of said laminar piece and through said bottom perforation.

10. A medical electrode according to claim 7, wherein the connector is connected to said radial extension and is a Stillson wrench type connector having a back end comprising a supporting non-skid circular platform with a center having an electrical connector.

11. A medical electrode according to claim 7, wherein the connector is a hook type connector having a circular base with a bottom face including sharp end bosses thereon.

* * * * *

UNITED STATES PATENT AND TRADEMARK OFFICE
CERTIFICATE OF CORRECTION

PATENT NO. : 5,197,471

DATED : March 30, 1993

INVENTOR(S) : SERVIO T. A. OTERO

It is certified that error appears in the above-identified patent and that said Letters Patent is hereby corrected as shown below:

On the Title page, item [76]
Change the name of the inventor to read:

--SERVIO T. AÑEZ OTERO--

Signed and Sealed this

Ninth Day of November, 1993

Attest:

BRUCE LEHMAN

*Attesting Officer*    *Commissioner of Patents and Trademarks*